United States Patent

Lo

[11] Patent Number: 4,960,896
[45] Date of Patent: Oct. 2, 1990

[54] PROCESS FOR THE PREPARATION OF 5-CHLORO AND 5-BROMO-2-HYDROXYNICOTINIC ACIDS

[75] Inventor: Young S. Lo, Richmond, Va.

[73] Assignee: A. H. Robins Company, Inc., Richmond, Va.

[21] Appl. No.: 120,488

[22] Filed: Nov. 13, 1987

Related U.S. Application Data

[63] Continuation-in-part of Ser. No. 801,725, Nov. 26, 1985, abandoned.

[51] Int. Cl.$^5$ .................. C07D 213/72; C07D 213/61
[52] U.S. Cl. .................................... 546/298; 546/296; 546/345
[58] Field of Search ................. 546/296, 298, 345

[56] References Cited

U.S. PATENT DOCUMENTS 4,716,281 12/1987 Goddard ............................ 546/345

OTHER PUBLICATIONS

Fieser's Reagent for Org. Synthesis, vol. 5, p. 322 (1975) and vol. 6, p. 543 (1977).
Klingsberg, Heterocyclic Compounds–Pyridine and its Derivatives, Part III (1966) pp. 646–659.
Morrison et al., Org. Chem. 3rd Ed., pp. 1013–1014.
Bachman et al., J. Am. Chem. Soc. 70, 238(1948) pp. 2381–2384.
Klingsberg, Heterocyclic Compounds–Pyridine and its Derivatives, Part II (1961) pp. 306–310.

Primary Examiner—John M. Ford
Assistant Examiner—J. Richter

[57] ABSTRACT

A process for the preparation of 5-halo-2-hydroxynicotinic acids having the formula:

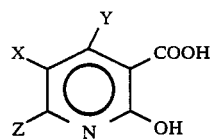

wherein X is chlorine or bromine, Y and Z are selected from hydrogen, loweralkyl or loweralkyl, is described wherein a corresponding 2-hydroxynicotinic acid is halogenated with alkali-metal hypohalite in a strongly alkaline solution pH 12 and above. Certain aspects of the isolation of the product are directed to avoiding replacement of the carboxy group with halogen.

10 Claims, No Drawings

PROCESS FOR THE PREPARATION OF 5-CHLORO AND 5-BROMO-2-HYDROXYNICOTINIC ACIDS

REFERENCE TO PARENT APPLICATION

This application is a continuation-in-part of U.S. application Ser. No. 801,725 filed on Nov. 26, 1985 now abandoned.

BACKGROUND OF THE INVENTION (1) Field of Invention

The present invention is concerned with a novel economical process for the preparation of certain 5-halo-2-hydroxynicotinic acids by halogenation of 2-hydroxynicotinic acids with alkali-metal hypohalites in strongly alkaline solution. The reaction conditions and isolation procedures avoid substantial loss due to formation of 3,5-dihalo-2-hydroxypyridines caused by replacement of the carboxy group with a halogen atom.

(2) Information Disclosure Statement

Prior to the present invention, the halogenation of 2-hydroxynicotinic acids to produce 5-halo-2-hydoxynicotinic acids was not disclosed in the literature.

The chlorination of 2-hydroxypyridine has recently been disclosed by A. R. Katritsky et al. in the J. ORG. CHEM. (1984) 49: pp 4784–4786 but not prior to the present invention. In that disclosure 5-chloro-2-pyridine which is equivalent to 5-chloro-2-hydroxypyridine was prepared by reacting 1 equivalent of 2-pyridone (the same as 2-hydroxypyridine) with 10 equivalents of sodium hypochlorite. In contrast, the 2-hydroxypyridines of the present invention are substituted in the three position by a carboxy radical.

The preparation of 5-chloro-2-hydroxynicotinic acid from 5-amino-2-hydroxynicotinic acid, hydrochloric acid and sodium nitrate is described in U.S. Pat. Nos. 3,709,991 and 3,738,990.

H. M. Gilow in J. ORG. CHEM. (1974) vol. 39, 3481–3486 has reported on kinetics of bromination of some pyridinium ions such as 2,6-dimethylpyridinium to produce 3-bromo-2,6-dimethylpyridine using hypobromous acid in aqueous perchloric acid.

Chlorination of pyridinecarboxylic acids with thionyl chloride was discussed by E. Klingsberg in Chemistry of Heterocyclic Compound-Pyridine and Its Derivatives—Part Two page 308 (1961) published by Interscience Publishers, Inc. N.Y. and London. However, thionyl chloride would not be an appropriate chlorinating agent for 2-hydroxynicotinic acid enroute to 5-chloro-2-hydroxynicotinic acid inasmuch as it is known that hydroxyl groups are readily replaced with a chloro radical with this reagent. Klingsberg, ibid p. 307, states hydrogen chloride-hydrogen peroxide halogenation of hydroxypyridines is said to give good yields of isomer free products. Contrariwise in the instance of 2-hydroxynicotinic acid I found, as can be seen in my preliminary Trial B and C described hereinbelow, poor yields of the desired product and substantial loss occurred when hydrogen chloride and hydrogen peroxide were used due to replacement of the carboxy group with chlorine to give 3,5-dichloro-2-hydroxypyridine and other multiple halogen compounds.

The solid products of the process of this invention i.e., compounds of Formula I, are useful as hypolipidemics as described in U.S. Pat. Nos. 3,709,991 and 3,738,990. The compounds are also useful for the preparation of fused aromatic oxazepinones such as are described in U.S. Pat. No. 4,592,866 derived from application Ser. No. 746,091, filed June 18, 1985, which oxazepinones are useful as antihistaminics. Halogenation of 2-hydroxynicotinic acids using metal hypohalite was disclosed in the latter patent.

(3) Preliminary Experimental Trials

The following experimental trials A to G describe my early unsuccessful attempts to find an economical procedure for preparing 5-halo-2-hydroxynicotinic acid from 2-hydroxynicotinic acids.

TRIAL A

Chlorine added to a Basic Solution of 2-Hydroxynicotinic Acid

To an aqueous sodium hydroxide solution prepared by adding 28 g (0.35 mole) of 50% sodium hydroxide to 70 ml of water was added 7 g (0.05 mole) of 2-hydroxynicotinic acid. The resulting clear solution was chilled in an ice bath to 4° C. and chlorine gas was slowly bubbled into the solution for 55 minutes during which time the temperature was allowed to rise to 28° C. The solution was slightly basic and solids has precipitated. Chlorine addition was stopped and the mixture was acidified. Mass spectroscopy analysis showed the product to be mainly 3,5-dichloro-2-hydroxypyridine. Thin-layer chromatography using ethyl acetate-methanol-ammonium hydroxide in 3:1:1 volume ratio on silica gel showed a trace of starting 2-hydroxynicotinic acid and a trace of 5-chloro-2-hydroxynicotinic acid were present along with compounds having multiple halogens on a hydroxypyridine ring similar to that described in the following Trial B - Fraction 3.

TRIAL B

Hypochlorous Acid as Provided By Hydrogen Peroxide and Concentrated Hydrochloric Acid In Solution with 2-Hydroxynicotinic Acid To a solution of 42.5 g (0.3 mole) of 2-hydroxynicotinic acid in 212.5 ml of 37% hydrochloric acid (0.3 mole) was added dropwise 46 ml of a 30% aqueous solution of hydrogen peroxide (0.45 mole) at 25°±3° C. using an ice bath to control the temperature over a 10 minute period. The mixture was seeded with crystals from a previous trial. After 5-10 min. some crystals developed and after 1.5 hr precipitate was collected and rinsed three times with water and dried to give 16.75 g (Fraction 1) (32% yield) of crude 5-chloro-2-hydroxynicotinic acid containing 5-7% starting 2-hydroxynicotinic acid and some 3,5-dichloro-2-hydroxypyridine. After about 4 hr total time from the start, an additional 23 ml of 30% hydrogen peroxide was added to the mother liquor at 25°-30° C. At the 5th hour another 23 ml (0.22 mole) of 30% hydrogen peroxide was added. The solid was then collected and rinsed with water and dried to give 3.77 g (Fraction 2) (7.6% of yield) of crude 5-chloro-2-nicotinic acid containing 10-20% 3,5-dichloro-2-hydroxypyridine and a trace of starting material. The mother liquor was stirred overnight. No new precipitate was present. The mother liquor was then combined with rinsings from Fractions 1 and 2 and the resulting solution was extracted 3 times with methylene chloride. The combined methylene chloride layers were back washed with water, dried and evaporated to give 5.5 g of solid (Fraction 3). Analysis of Fraction 3 by $^1$HNMR gave many signals. Chemical Ionization Mass Spectroscopy analysis showed compounds m/e 214, 216, 218, 220 corresponding to compounds with multiple (2–3) halogen atoms on pyridine ring. For the trial as a whole, the total yield of 5-chloro-2-hydroxynicotinic acid was about 35% of theory considering the impurities and yield of polychlorinated impurities was about 10% on a theoretical mole base.

TRIAL C

Hypochlorous Acid as Provided By Hydrogen Peroxide and Concentrated Hydrochloric Acid in Solution with 2-Hydroxynicotinic Acid 2-Hydroxynicotinic acid was treated with hypochlorous acid derived from mixing concentrated hydrochloric acid and hydrogen peroxide by the following procedure:

A solution of 14 g (0.10 mole) of 2-hydroxynicotinic acid in 70 ml of 37% hydrochloric acid was added dropwise to 16 ml of a 30% aqueous solution of hydrogen peroxide (0.15 mole), keeping the temperature of the reaction mixture between 23°–45° C. (about ⅔ of the acid solution had been added in about 9 min and the remainder was added at a slower rate, total reaction time allowed being about 2 hr). The solid which precipitated was separated from the mother liquor by filtration, rinsed with water, and dried under vacuum to give the first crop, 24.8 g solid (37.7%). To the mother liquor was added 16 ml of 30% hydrogen peroxide (0.8 mole) and the mixture was stirred overnight. The precipitate which formed in the mother liquor was separated by filtration and rinsed and dried under vacuum to give a second crop of 1.38 g solid (8.0%). The total yield of title compound was 26.2 g for an overall yield of 45.7% of 5-chloro-2-hydroxy-3-pyridinecarboxylic acid. A substantial amount of 3,5-dichloro-2-hydroxypyridine was present in the mother liquor.

TRIAL D

Sodium Hypochlorite - No Excess Base in Solution With 2-Hydroxynicotinic Acid

A mixture of 7 g (0.05 mole) of 2-hydroxynicotinic acid in a 5% solution of sodium hypochlorite, 140 ml (0.094 mole), was stirred overnight at room temperature. Concentrated hydrochloric acid was added until the mixture became acidic. Precipitated solid was separated by filtration, rinsed 3 times with water, and air dried for 72 hr to give 4.42 g of solid. The solid was triturated 3 times with 6N hydrochloric acid and 3 times with water. The solid was dried under vacuum to give 2 g of product estimated by MS-CI to contain about 20% of starting 2-hydroxy-3-pyridincarboxylic acid.

Based on the $^1$HNMR analysis of the 4.42 g of solids initially obtained, the ratio of starting 2-hydroxynicotinic acid to product title compound was 1:1 and the yield of title compound was calculated to be 25.6%.

TRIAL E

Sulfuryl Chloride In Methylene Chloride Solvent With 2-Hydroxynicotinic Acid

A mixture of 2.0 g (0.014 mole) of 2-hydroxynicotinic acid and 6 ml of sulfuryl chloride in 16 ml of methylene chloride was heated at reflux for 2 hr. Thin-layer chromatography using ethyl acetate-methanol-ammonium hydroxide (29%) in a 4:1:1 volume ratio on silica gel showed a faint trace of 5-chloro-2-hydroxynicotinic acid.

TRIAL F

Sulfuryl Chloride In 1,1,1-Trichloroethane Solvent With 2-Hydroxynicotinic Acid

To a suspension of 2.0 g (0.014 mole) of 2-hydroxynicotinic acid in 16 ml of 1,1,1-trichloroethane heated at reflux, was added dropwise 6 ml (0.075 mole) of sulfuryl chloride over a 3 minute period. Thin-layer chromatography (TLC) using ethyl acetate-methanol-ammonium hydroxide (29%) in 4:1:1 vol ratio with silica gel on a sample of the reaction mixture showed presence of only a trace of 5-chloro-2-hydroxynicotinic acid.

Two ml of dimethylformamide was added to the reaction mixture and heating was continued for 2 additional hours. TLC of a sample again showed only a trace of 5-chloro-2-hydroxynicotinic acid.

An additional 6 ml of sulfuryl chloride was added to the reaction mixture and heating was continued for another hour. Volatiles were evaporated, and water was added and evaporated off and water was added again. The aqueous portion was decanted and the residue was dissolved in methanol-water and evaporated to give a brown residue which when subjected to TLC using ethyl acetate-methanol-ammonium hydroxide in a 3:1:1 ratio on silica gel showed a trace of 5-chloro-2-hydroxynicotinic acid, some starting material and 4 other major impurities.

TRIAL G

Sulfuryl Chloride In Excess as Solvent With 2-Hydroxynicotinic Acid

A suspension of 4.0 g (0.028 mole) of 2-hydroxynicotinic acid in 20 ml of sulfuryl chloride was heated to reflux for 1 hr. A sample was subjected to TLC using ethyl acetate-methanol and ammonium hydroxide in 4:1:1 vol ratio on silica gel. Spots showed mainly starting material and a trace of 5-chloro-2-hydroxynicotinic acid. The reaction mixture had become a thick paste due to decomposition of sulfuryl chloride.

An additional 20 ml of sulfuryl chloride was added and heating continued at reflux for another 1.5 hr at which time TLC testing showed mainly starting material.

An additional 20 ml of sulfuryl chloride was added and heating continued for another hr. TLC showed mainly starting material, some 5-chloro-2-hydroxynicotinic acid and at least 5 other spots (impurities).

SUMMARY OF THE INVENTION

The invention is especially concerned with economical procedures for halogenation of 2-hydroxynicotinic acids of Formula II to give single halogenation products, the 5-halo-2-hydroxynicotinic acids of Formula I and the recovery thereof from the reaction mixture without replacement of the carboxy group by a halo radical. Among the features of the process, described more in detail hereinbelow under "Detailed Description of the Invention" which I have discovered and which make the process economically feasible with yields as high as about 95% of theory are the following:

(a) Use of strongly alkaline solution (pH 12 and above) as medium for the halogenation with alkaline-metal hypohalites increases reaction rate and yield and minimizes multiple halogenation.

(b) minimizing contact of dissolved 5-halo-2-hydroxynicotinic acid products (Formula I) with halogenating agent under acid conditions (below pH 7) during isolation avoids substantial loss to formation of 3,5-dihalo-2-hydroxypyridine caused by replacement of the carboxy group with a halogen radical. This includes avoidance of use of free hypohalous acid and free chlorine under acidic conditions (i.e., below pH 7). Also included is use of minimal time for acidification and precipitation below pH of 7. The use of a reducing agent to decompose the halogenating agent prior to acidification is a preferred procedure for preventing contact of dissolved 5-chloro-2-hydroxynicotinic acid products with halogenating agent and thereby minimizing loss to 3,5-dihalo-2-hydroxypyridine.

Prior to these discoveries and during my early trials described supra, it was not known whether conditions could be found under which replacement of the carboxy group by halogen could be found. Certain relationships of pH to solubility and stability which I have discovered are outlined in Table 1 and are useful in understanding and practicing the invention.

TABLE 1 pH Relationships (Hypohalite Chlorination)

| pH of Reaction mixture | Properties of 5-Halo-2-Hydroxynicotinic Acid In Relation to Reaction Mixture Containing Halogenating Agent | |
|---|---|---|
| | Solubility | Stability |
| 12 and above (MOX + 1–5 moles MOH)* | Soluble | Stable |
| 7–12 (MOX + 0–1) | Soluble | Stable |
| 5–7 | Soluble | Unstable (a) |
| 3–5 | Precipitating Range | Precipitate Stable; Dissolved product unstable (a) |
| Below 1 (HCl + H₂O₂) | Soluble | Unstable (b) |

(a) Carboxy group of 5-halo-2-hydroxynicotinic acid exchanges with another halo group to give 3,5-dihalo-2-hydroxypyridine.
(b) Carboxy group of both starting material and product readily replaced with halo. Other multiple halogenations also occur.
*MOX is alkali-metal hypohalite; MOH is alkali-metal base.

5-Halo-2-hydroxynicotinic acids prepared by the novel process of the invention have the formula:

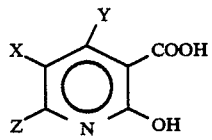

Formula I wherein X is chlorine or bromine; Y and Z are selected from hydrogen, loweralkyl or loweralkoxy.

Aqueous mixtures prepared in the novel process of the invention from which compounds of Formula I are isolated contain therein the equivalent of 5-halo-2-hydroxynicotinic acid compounds having the formula:

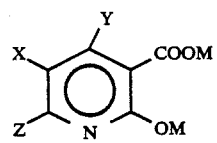

Formula II wherein X, Y and Z are defined under Formula I and M is alkali-metal.

In the process of the invention, 5-halo-2-hydroxynicotinic acid salts (Formula II) are obtained in solution by halogenating 2-hydroxynicotinic acid compounds having the formula:

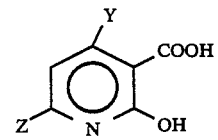

Formula III using alkali-metal hypohalites and under strongly alkaline conditions.

The following equation sets forth the chemistry involved in the chlorination reaction and the precipitation:

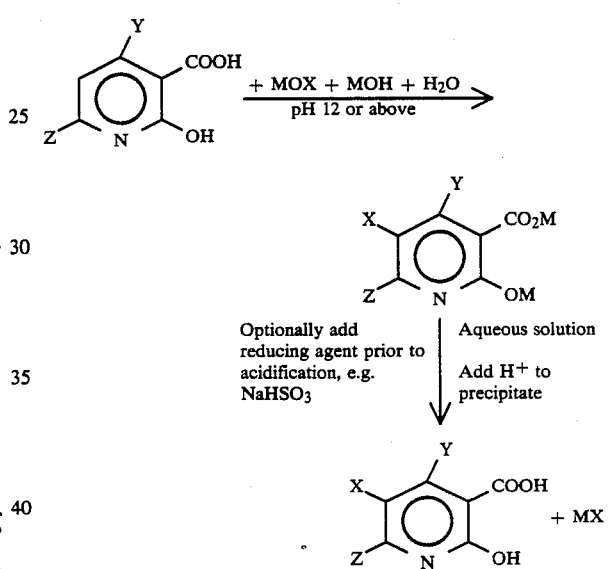

In the foregoing equation, X is chlorine or bromine; Y, Z and M are as defined under Formulas I and II above. M is preferably sodium.

Alkali-metal hypohalite solutions may be prepared in the reaction vessel prior to addition of 2-hydroxynicotinic acid by reacting an alkali-metal hydroxide and halogen gas as was done in certain of the examples hereinbelow. The equation is $$2MOH + X_2 \rightarrow MOX + MX + H_2O$$

wherein M is alkali-metal and X is chlorine or bromine.

Extra base needed to bring the pH to 12 or above may be added as excess during hypohalite preparation or afterward.

In the further definition of symbols in the formulas hereof and where they appear elsewhere throughout this specification and the claims, the terms have the following significance.

The term "loweralkyl" as used herein, unless otherwise specified, includes straight and branched chain radicals of up to eight carbons inclusive and is exemplified by such groups as methyl, ethyl, propyl, isopropyl, butyl, sec.-butyl, tert.-butyl, amyl, isoamyl, hexyl, heptyl and octyl radicals and the like. The term "loweralkoxy" has the formula -O-loweralkyl.

The term "halo" as it applies to the general term 5-halo-2-hydroxynicotinic acids or compounds refers to chlorine or bromine. The "alkali-metal hypohalites" are sodium, potassium and lithium hypochlorite and hypobromite.

The terms "5-chloro-2-hydroxy-3-pyridinecarboxylic acid" and "5-chloro-2-hydroxynicotinic acid" are synonymous and are used interchangeably throughout the specification and claims. The same analogy applies to other halogen homologs and analogs within the scope of the defined herein.

The term "strongly alkaline" refers to pH range of 12 or above.

DETAILED DESCRIPTION OF THE INVENTION

The novel process of the present invention in its most comprehensive aspect comprises the steps of:

Step 1, reacting a 2-hydroxynicotinic acid compound having the formula:

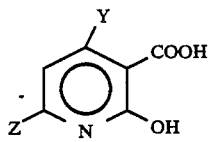   III wherein Y and Z are selected from hydrogen, loweralkyl or loweralkoxy, in aqueous solution containing a hypohalite salt having the formula:

MOX and a base having the formula:

MOH wherein M is an alkali-metal ion and X is chlorine or bromine and said base is present in amount sufficient to raise the pH of the said aqueous solution to at least 12 to give a solution of a compound having the formula:

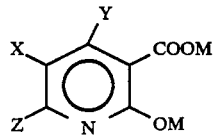   II wherein X, Y and Z have the starting values of the reactants and M is alkali-metal;

Step 2, optionally, but preferably, adding to the solution prepared in Step 1 an amount of reducing agent sufficient in amount to substantially eliminate the halogenating agents derived from said MOX, i.e., hypohalous ion and free chlorine, from the solution;

Step 3, mixing the solution obtained in Steps 1 or 2 with strong acid in an amount sufficient to substantially precipitate the 5-halo-2-hydroxynicotinic acid having the formula:

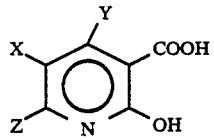   I wherein X is chloro or bromo and Y and Z have the starting values and separating the precipitate from the slurry.

Step 1 is a novel economic method of preparing a solution of the 5-chloro or 5-bromo-2-hydroxynicotinic acid alkali-metal salts of Formula II from which free acids may be obtained. Step 1 by itself is therefore an inventive entity or it may be joined by Steps 2 and/or 3 to provide the more comprehensive process of Steps 1, 2 and 3 combined or Steps 1 and 3 combined.

In further reference to the process and process steps of the invention summarized above as they apply to the preparation of solutions of compounds of Formula II and separated solid compounds of Formula I, the following further description is applicable.

In Step 1, temperatures of about 0° to 50° C. are suitable, preferably 0°–25° C. for carrying out the halogenation. At least 1 mole of base per mole of starting 2-hydroxynicotinic acid compound along with the hypohalite is used to provide alkalinity (pH 12.0 or above) to drive the reaction to completion within a reasonable time period. Optimum yields are obtained when the ratio of base to 2-hydroxynicotinic acid is about 1.0 to 3.0 which ratio range is preferred. Above about a ratio of 5:1 mole of base per mole of 2-hydroxynictonic acid compound, the process becomes uneconomical.

A further preferred procedure in carrying out Step 1 is to add the hypohalite in two portions allowing a period of time of about 8–48 hr to lapse between additions. Sodium, potassium or lithium hypohalites may be used singly or a combination of 2 or more may be used, e.g. sodium and potassium hypohalites for example could be used. Sodium hypohalites are preferred halogenating agents.

In optional Step 2 reducing agent is added to reduce hypohalous ion and or halogen, a suitable indication being when an acidified strip of starchiodide paper no longer shows the presence of halogenating agent. Any reducing agent which does not interfere with isolation of this product or does not appreciably increase cost is suitable. Among the suitable reducing agents are metal bisulfite salts, preferably sodium or potassium bisulfite, metal salts of thiosulfate, metal salts of hypophosphite, metal salts of hydrosulfite, stannous halide, tin, zinc, amalgams, hydrazine, diimide, formic acid and salts thereof, metal salts of disulfide, metal salts of hydrazide, etc. Employment of this step (Step 2) prevents loss of about 5% of 5-halo-2-hydroxynicotinic acids in further replacement of the carboxy group to give 3,5-dihalo-2-hydroxypyridine impurity.

In Step 3, the reaction mixture is preferably introduced into the strong acid solution rather than vice versa to bring about the precipitation of the product 5-halo-2-hydroxynicotinic acid in a crystal form which can be readily filtered from the mixture. When Step 2 is omitted it is imperative for optimum yield to employ this preferred procedure of mixing the reaction mixture into the strong acid (pH below 3 at all times) inasmuch as the carboxy group of the product is readily replaced by halogen while the product 5-halo-2-hydroxynicotinic acid is still in solution in the presence of halogenating agent as the pH is dropped to pH 7 and below. Illustrative of suitable strong acids are hydrochloric, sulfuric, phosphoric and formic acids. Solids may be separated by filtration and centrifugation.

The following examples illustrate various aspects of the process of the invention; the scope of the invention is not limited by the examples, however.

EXAMPLE 1

5-Bromo-2-hydroxy-3-pyridinecarboxylic acid

To a solution of 10 g (0.07 mole) of 2-hydroxynicotinic acid in 16.8 g of 50% sodium hydroxide (0.21 mole) diluted with 25 ml of water was added 200 ml of sodium hypobromite solution prepared by adding 13.6 g (0.17 mole) of bromine to a solution of 20.16 g of 50% sodium hydroxide (0.25 mole) in 125 ml of water at 0° C. diluted to 400 ml. After 24 hrs of stirring at room temperature, another 100 ml portion of the above sodium hypobromite solution was added and the reaction solution was stirred for another 24 hr. The reaction solution was cooled in an ice bath and acidified carefully with 12N hydrochloric acid to give a preicpitate which was collected by filtration. Recrystallization from isopropyl alcohol alcohol gave 9.7 g (63.5%) of product. A sample was further recrystallized from 95% ethanol, m.p. 245° C.

Analysis: Calculated for $C_6H_4NO_3Br$: C: 33.06; H, 1.85; N, 6.42; C, 32.98; H, 1.83; N, 6.44.

EXAMPLE 2

5-Chloro-2-hydroxy-3-pyridinecarboxylic acid

2-Hydroxynicotinic acid was chlorinated in aqueous solution by using two additions in sequence (time interval between) of freshly prepared sodium hypochlorite solution resulting from reaction of chlorine and excess sodium hydroxide. The overall molar ratio of 2-hydroxynicotinic acid:sodium hypochlorite:excess sodium hydroxide in the chlorinating reaction was about 1:1.6:2.25 considering the totals in both additions. The detailed procedure used was as follows:

Sodium hydroxide, 336 g of 50% solution (4.2 mole) in 1 kg of ice was treated with bubbling chlorine gas while stirring until 78 g (1.1 mole) of chlorine was taken into the solution. To the resulting cold, basic sodium hypochlorite solution was added 142 g (1.0 mole) of 2-hydroxynicotinic acid in one portion. Within ½ hr the temperature had risen to 35° C. and dissolution had occurred. The mixture was stirred overnight after which time $^{13}$CNMR analysis indicated the ratio of starting material to desired product (as the disodium salt) was about 30:70%. Another solution of basic sodium hypochlorite was prepared by the above procedure by absorbing 35 g (0.5 mole) of chlorine gas in a mixture of 100 g of 50% solution (1.25 mole) of sodium hydroxide and 278 g of ice. This hypochlorite solution was added to the main reaction mixture and stirring was continued overnight. $^{13}$CNMR analysis indicated the starting 2-hydroxynicotinic acid had all reacted and the desired 5-chloro-2-hydroxynicotinic acid was present as the disodium salt. Sodium bisulfite, 14 g was added and stirring was continued for 1.5 hr. The reaction mixture was gradually added to a cooled, stirred solution of 337 ml of concentrated (37%) hydrochloric acid. The maximum temperature of the acidified mixture was 25° C. The yield of title compound on separation and drying was 146 g (84%).

The $^1$HNMR spectrum was obtained in DMSO-d$_6$ as follows:

| Chemical Shifts | Assignments |
| --- | --- |
| 13.20 ppm (broad singlet) | 2 protons |
| 8.20 ppm (multiplet) | 3 protons |

The $^{13}$CNMR spectrum was obtained in DMSO-d$_6$:

| Chemical Shifts | Assignments |
| --- | --- |
| 113.86 ppm | the beta-carbon bearing the carboxyl group |
| 117.76 ppm | the meta-carbon bearing the chlorine atom |
| 140.01 ppm | the unsubstituted carbon para to the pyridine nitrogen |
| 145.35 ppm | the unsubstituted carbon ortho to the pryidine nitrogen |
| 163.41 ppm} | the carboxyl carbon and the |
| 164.12 ppm} | ortho carbon bearing the hydroxyl group |

Scan of the $^1$HNMR chart showed a trace amount of 3,5-dichloro-2-hydroxypyridine was present in the dry product. See Example 3 for the method of estimating the amount.

EXAMPLE 3

5-Chloro-2-hydroxy-3-pyridinecarboxylic acid

2-Hydroxynicotinic acid was chlorinated in aqueous solution by using 2 additions in sequence (time interval between) of freshly prepared aqueous sodium hypochlorite solution resulting from reaction of chlorine and excess sodium hydroxide. The overall molar ratio of hydroxynicotinic acid:sodium hypochlorite:excess hydroxide in the chlorinating reaction was about 1:1.5:2.4 considering the totals in both additions. The detailed procedure used was as follows:

Sodium hydroxide, 10.05 kg of 50% solution (125.6 mole) in 30 kg of ice was treated with bubbling chlorine gas while stirring until 2.22 kg (31.3 mole) of chlorine was taken into the solution. To the resulting basic sodium hypochlorite solution was added 4.26 kg (30 mole) of 2-hydroxynicotinic acid. External cooling with tap-water was used to keep the temperature between 20°–35° C. Stirring was continued over the weekend (72 hr) after which time $^{13}$CNMR analysis showed that about 70% of the 2-hydroxynicotinic acid was chlorinated. Another solution of basic sodium hypochlorite solution was prepared by the above procedure by absorbing 1.05 kg (14.8 mole) of chlorine gas in a mixture of 3.0 kg of 50% solution (37.5 mole) of sodium hydroxide and 8.3 kg of ice. This hypochlorite solution was added to the main reaction mixture and stirring was continued for about 12 hr, after which time $^{13}$CNMR indicated no 2-hydroxynicotinic acid remained. A solution of 104 g (1.0 mole) of sodium bisulfite in 300 ml of water was added to destroy the remaining sodium hypochlorite. The reaction mixture was added gradually to 9.9 liters (119 mole) of concentrated hydrochloric acid containing 2 liters of isopropyl alcohol (to control foam), keeping temperature between 13°–23° C. The mixture was cooled and the precipitate was collected by filtration, washing with a small amount of water followed by 2 liters of acetone. The precipitate was dried to give 4.44 kg (85%) of the title compound, m.p. starts at 245° C. and decomposes at 250° C. Analysis of the 1HNMR chart showed that approximately 4% of the product was 3,5-dichloro-2-hydroxypyridine. This was done by 1HNMR (DMSO-d6 ppm), integrating the area under the curves to determine relative amounts under the appropriate signals which are for 2-hydroxy-5-chloronicotinic acid: 8.25 (multiplet) and for 3,5-dichloro-2-hydroxypyridine: 7.90 to 7.60 (quartet).

EXAMPLE 4

5-Chloro-2-hydroxy-3-pyridinecarboxylic acid

To an agitated solution of 216.0 g (5.4 mole) of sodium hydroxide pellets in 2.25 liters of 5% (1.51 moles) sodium hypochlorite solution was added 150.0 g (1.08 mole) of 2-hydroxynicotinic acid. Temperature of the mixture was 20°-32° C. After 4 hr mass spectrographic analysis showed some starting 2-hydroxynicotinic acid was present. An additional liter of 5% (0.67 moles) of sodium hypochlorite solution was added and stirring was continued overnight. Starting 2-hydroxynicotinic acid was no longer present. Slow acidification with 690 ml of concentrated of the reaction mixture under agitation over a 1.25 hr period resulted in conversion to a mass of porous fluffy salt crystals. As more acid was added severe bubbling occurred and half of the reactor contents had to be removed. Both portions were completely acidified, the total of additional acid being 100 ml concentrated hydrochloric acid. The mixture was filtered on a large sintered glass funnel and crystals became gooey and difficult to handle. Once the filter cake had reached a mud-like stage, it was slurried in 500 ml of 6N hydrochloric acid and refiltered. The filter cake was rinsed with 350 ml of water and subjected to vacuum for several hours. The filter cake was rinsed first with 300 ml of 1:1 isopropyl ether/isopropyl alcohol then with 300 ml of 3:1 isopropyl ether/isopropyl alcohol and subjected to vacuum filtration for several hours. The crystals were desicated under vacuum using a heat lamp. The weight of dry crystals was 84.5 g (45.1%). However 1HNMR analysis indicated that the product contained 10-12% impurity≠(3,5-dichloro-2-hydroxypyridine). See Example 3 for the method of computing impurity. The original filtrate also contained this impurity.

EXAMPLE 5

5-Chloro-2-hydroxy-3-pyridinecarboxylic acid

To an agitated solution of 216.0 g of sodium hydroxide pellets in 2.25 liters of 5% (1.51 moles) sodium hypochlorite solution was added 150.1 g (1.08 mole) of 2-hydroxynicotinic acid. Temperature of the reaction mixture was 20° C. Four hours later 750 ml of 5% (0.50 mole) of sodium hypochlorite solution was added and stirring was continued overnight. The reaction mixture was mixed with 12N hydrochloric acid in an agitated vessel in such a manner that the receiving solution was always strongly acid and temperature was kept below 20° C. with an ice bath. The amount of 12N acid used was 600 ml. The mixture was readily filtered on a sintered glass suction funnel. The crystalline filter cake was washed with 800 ml of water followed by 800 ml of 1:1 isopropyl ether/isopropyl alcohol. Crystals were powdery when dry. The weight of dry crystals was 153.2 g (81.8% yield). Analysis by 1HNMR showed the dried product contained no starting material and contained about 5% of 3,5-dichloro-2-hydroxypyridine. See Example 3 for method of computing impurity.

EXAMPLE 6

5-Chloro-2-hydroxy-3-pyridinecarboxylic acid

To an agitated solution of 216.0 g of sodium hydroxide pellets in 2.25 liters of 5% (1.51 moles) of sodium hypochlorite solution was added 150.4 g of 2-hydroxynicotinic acid. Temperature of the reaction mixture was 19° C. Three hours later 750 ml (0.50 mole) of sodium hypochlorite was added and stirring was continued overnight. The reaction mixture was mixed with 12N hydrochloric acid in an agitated vessel in such a manner that the receiving solution was always strongly acid and temperature was kept below 20° C. with an ice bath. The amount of 12N acid used was 600 ml. The mixture was readily filtered on a sintered glass suction funnel. The crystalline filter cake was washed with 600 ml of water followed by 800 ml of 1:1 isopropyl ether/isopropyl alcohol. Weight of the dry crystals was 143.5 g (76.6% yield). Analysis by 1HNMR analysis showed the dried product contained no starting material and about 5% 3,5-dichloro-2-hydroxypyridine. See Example 3 for method of computing impurity.

EXAMPLE 7

5-Chloro-2-hydroxy-3-pyridinecarboxylic acid

Sodium hypochlorite solution was prepared by first adding 35.41 kg (442.6 mole) of 50% sodium hydroxide solution to 44 kg of flaked ice in a jacketed vessel having external circulating coolant; then adding 61.6 kg more flaked ice and introducing 7.87 kg (110.9 mole) of chlorine below the surface, all with agitation. To the sodium hypochlorite solution was added, portionwise, 15.0 kg of 98% purity (105.7 mole) 2-hydroxynicotinic acid (solids). The reaction temperature rose to 35° C. during the addition of the solids. Coolant was removed from the jacket and the mixture was stirred overnight at room temperature. A sample was withdrawn and acidified with concentrated hydrochloric acid to give precipitate which when analyzed by 1HNMR showed 75:25 ratio of title compound to starting 2-hydroxynicotinic acid. A second solution of sodium hypochlorite prepared as above from 10.57 kg of 50% sodium hydroxide solution (132.1 mole), 29.1 kg of ice and 3.65 kg (51.5 mole) of chlorine was added to the reaction mixture and the mixture was stirred overnight. This time a sample precipitated with concentrated hydrochloric acid showed no starting 2-hydroxynicotinic acid was present. Sodium bisulfite, 208 g (2.0 mole) was added to decompose unreacted excess sodium hypochlorite. Seven liters of isopropyl alcohol was then added to reduce expected foaming in the next step. The reaction mixture was added slowly to 41.48 kg (34.9 liters, 419.3 mole) of concentrated hydrochloric acid using external cooling to keep the mixture at 15°-25° C. pH of the mixture was 1.0. The slurry was filtered and the filter cake was washed with about 20 liters of water followed by 7 liters of acetone. The crystals were dried at 100° F. to a water content of about 5%; then milled and redried at 120° F. to a water content of 0.4%. The amount of crystals obtained was 17.42 kg (95.6% yield). 1HNMR analysis as described in Example 3 showed a trace of 3,5-dichloro-2-hydroxypyridine was present.

EXAMPLE 8

5-Chloro-2-hydroxy-3-pyridinecarboxylic acid

Sodium hypochlorite solution was prepared by first adding 40.2 kg (500 moles) of 50% sodium hydroxide solution to 50 kg of flaked ice in a jacketed vessel having external coolant; then adding 70 kg more ice and introducing 8.88 kg (125 moles) of chlorine gas below the surface, all with agitation. Temperature of the hypochlorite solution was −8° C. To the hypochlorite solution was added, portion wise, 17.04 kg (120.0 mole) of 98% purity 2-hydroxynicotinic acid. The temperature of the reaction mixture rose to 27° C. After stirring overnight, a sample was withdrawn and neutralized with 37% hydrochloric acid to give precipitate which when analyzed by $^1$HNMR showed 80:20 ratio of title compound to starting 2-hydroxynicotinic acid. A second solution of sodium hypochlorite prepared as above from 12 kg of 55% sodium hydroxide solution (152.4 mole), 33 kg of ice and 4.15 kg (58.5 mole) of chlorine was added to the reaction mixture and the mixture was stirred overnight at room temperature. $^1$HNMR analysis showed no starting material was present. Sodium bisulfite, 416 g (4.0 mole) was added and the mixture agitated for about 5 min. Eight liters of 2-isopropyl alcohol was added to reduce expected foaming. The reaction mixture was then mixed gradually with concentrated 37% hydrochloric and keeping the temperature generally at 15°-23° C. with good agitation. The temperature of the acidified mixture was then cooled to 2° C. and filtered. The filter cake was washed with 15 liters of cold water followed by 8 liters of acetone. The solids were dried for 2 days at 80° F. and pressed through an 18 mesh screen. The crystals were then dried further in a vacuum oven at 125° F. to give 18.81 kg (90.1% yield) of title compound. $^1$NMR analysis by the procedure of Example 3 showed only a trace of 3,5-dichloro-2-hydroxypyridine was present.

What is claimed is:

1. A process for the preparation of a 5-halo-2-hydroxynicotinic acid compound selected from the group having the formula:

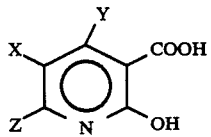

wherein X is selected from chlorine or bromine and Y and Z are selected from hydrogen, loweralkyl or loweralkoxy which comprises the steps of:

Step 1, reacting a 2-hydroxynicotinic acid compound having the formula:

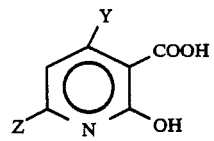

wherein Y and Z are selected from hydrogen, loweralkyl or loweralkoxy in aqueous solution containing both a hypohalite salt having the formula:

MOX and a base having the formula:

MOH wherein M is an alkali-metal ion selected from sodium, potassium or lithium and X is chlorine or bromine and said base is present in amount sufficient to raise the pH of said aqueous solution to at least 12 to give a solution containing a compound having the formula:

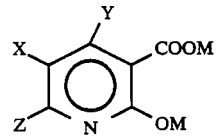

wherein X, Y and Z have the starting values of the reactants and M is alkali-metal;

Step 2, optionally adding to the solution prepared in Step 1, an amount of reducing agent sufficient in amount to eliminate hypohaous ion and free chlorine from said solution;

Step 3, mixing the solution obtained in Steps 1 or 2 with strong acid solution in an amount sufficient to substantially precipitate a said 5-halo-2-hydroxynicotinic acid and separating it from the slurry.

2. The process of claim 1 wherein in Step 1, the alkali-metal hypohalite used is sodium hypochlorite.

3. The process of claim 1 wherein in Step 1, the ratio of alkali-metal base to alkali-metal hypohalite used is about 1.0 to 3.0 moles of said base per mole of said hypohalite.

4. The process of claim 1 wherein in Step 1, 2-hydroxynicotinic acid is chlorinated to give 5-chloro-2-hydroxynicotinic acid alkali-metal salt in solution.

5. The process of claim 1 wherein in Step 1, 2-hydroxynicotinic acid is brominated to give 5-bromo-2-hydroxynicotinic acid alkali-metal salt in solution.

6. The process of claim 1 wherein in Step 2, the reducing agent used is a metal bisulfite salt.

7. The process of claim 1 wherein in Step 2 the reducing agent used is sodium bisulfite.

8. The process of claim 1 wherein in Step 3 the solution obtained in Steps 1 or 2 is added to and mixed into said strong acid solution maintaining pH of the receiving solution at pH 3 or below.

9. A process for the preparation of a solution of an alkali-metal salt of a 5-halo-2-hydroxynicotinic acid selected from the group having the formula:

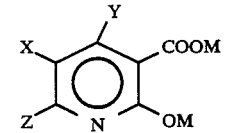

wherein X is selected from chlorine or bromine and Y and Z are selected from hydrogen, loweralkyl or loweralkoxy and M is alkali-metal which comprises reacting a 2-hydroxynicotinic acid compound having the formula:

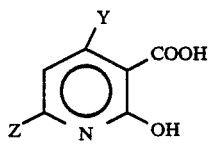

wherein Y and Z are selected from hydrogen, loweralkyl or loweralkoxy in aqueous solution containing a combination of hypohalite salt having the formula:

MOX and a base having the formula:

MOH wherein M is an alkali metal ion selected from sodium, potassium or lithium and X is chlorine or bromine and said base is present in amount sufficient to raise the pH of said aqueous solution to at least 12 to give a solution containing a said 5-halo-2-hydroxynicotinic acid salt.

10. In a process for halogenating a 2-hydroxynicotinic acid having the formula:

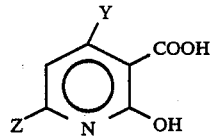

wherein Y and Z are selected from hydrogen, loweralkyl or loweralkoxy in aqueous solution with an alkali-metal hypochlorite: MOX and an alkali-metal base: MOH wherein M is alkali-metal and X is chlorine or bromine and said base being present in amount during reaction in amount sufficient to raise the pH of said solution to at least 12, the step of adding a reducing agent to decompose the halogenating agents prior to acidifying the reaction mixture to precipitate the halogenated product, a 5-halo-2-hydroxynicotinic acid having the formula:

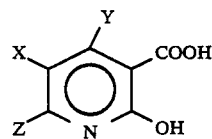

wherein Y and Z have their starting values and X is chlorine or bromine.

* * * * *